15

United States Patent [19]

Franken et al.

[11] Patent Number: 5,460,944
[45] Date of Patent: Oct. 24, 1995

[54] STORABLE PROTEIN SOLUTION

[75] Inventors: Norbert Franken, Starnberg; Nicholas Hoyle; Gunter Pappert, both of Tutzing, all of Germany

[73] Assignee: Boehringer Mannheim GmbH, Mannheim-Waldhof, Germany

[21] Appl. No.: 51,253

[22] Filed: Apr. 21, 1993

Related U.S. Application Data

[63] Continuation-in-part of Ser. No. 967,668, Oct. 28, 1992, abandoned.

[30] Foreign Application Priority Data

Oct. 28, 1991 [DE] Germany .......................... 41 35 542.3

[51] Int. Cl.$^6$ ................................................ G01N 33/535
[52] U.S. Cl. ....................... 435/7.9; 424/94.3; 435/27; 435/28; 435/188; 435/962; 436/826
[58] Field of Search ................................ 435/7.9, 27, 28, 435/188, 962; 424/94.3; 436/826

[56] References Cited

U.S. PATENT DOCUMENTS

| | | | |
|---|---|---|---|
| 4,169,012 | 9/1979 | Dawson et al. | 435/7.9 |
| 4,208,479 | 6/1980 | Zuk et al. | 435/7.9 |
| 4,299,916 | 10/1981 | Litman et al. | 435/6 |
| 4,394,512 | 7/1983 | Batz | 435/10 X |
| 4,448,882 | 5/1984 | Brodbeck et al. | 435/188 |
| 4,476,223 | 10/1984 | Buschek et al. | 435/188 |
| 4,543,326 | 9/1985 | Miyashita et al. | 435/188 |
| 4,757,016 | 7/1988 | Klenner et al. | 435/188 |
| 4,764,468 | 8/1988 | Wehner et al. | 435/188 |
| 4,826,776 | 5/1989 | Brandt et al. | 436/501 |
| 4,833,073 | 5/1989 | McNally et al. | 435/7 |
| 4,914,040 | 4/1990 | Lenz et al. | 436/175 |
| 5,075,221 | 12/1991 | Mauck et al. | 435/7.36 |
| 5,122,453 | 6/1992 | Martin et al. | 435/7.24 |
| 5,166,054 | 11/1992 | Nagui | 435/7.92 |

FOREIGN PATENT DOCUMENTS

| | | |
|---|---|---|
| 080304 | 6/1983 | European Pat. Off. . |
| 361088 | 4/1990 | European Pat. Off. . |
| 426552 | 5/1991 | European Pat. Off. . |
| 456309 | 11/1991 | European Pat. Off. . |
| 487301 | 5/1992 | European Pat. Off. . |

OTHER PUBLICATIONS

Sigma Chemical Co. 1988 Catalog. p. 306.
Good, N. E. et al. Hydrogen Ion Buffers for Biological Research. Biochemistry 5:467–477, 1966.
Windholz, M., ed. The Merck Index, 10th edition. Rathway, N.J.: Merck and Co., 1983, p. 71, entry 480.
Harlowe, E. et al. Antibodies: A Laboratory Manual. Cold Spring Harbor, N.Y.: Cold Spring Harbor Laboratory, 1988. p. 396.

Primary Examiner—Toni R. Scheiner
Assistant Examiner—Christopher L. Chin
Attorney, Agent, or Firm—Felfe & Lynch

[57] ABSTRACT

The present invention provides a storable POD conjugate solution, characterised by a pH value of 5.0 to 6.5, adjusted by means of an organic buffer substance with a concentration of 40 to 100 mmol/l, and 0.05 to 1.0 mol/l magnesium aspartate.

17 Claims, No Drawings

STORABLE PROTEIN SOLUTION

This application is a continuation in part of Ser. No. 967,668, filed Oct. 28, 1992 and now abandoned.

The present invention is concerned with storable conjugates of proteins and horseradish peroxidase (POD conjugates).

In DD 237327 are described proteins, heterocyclic azines and polyalcohols in a medium with a pH value of from 6.0 to 7.5 for the stabilisation of POD (HRP) conjugates. In EP-A 0 303 062, hydroysed chicken albumin and/or calf serum, polyvinylpyrrolidone and/or calcium propionate, ANS (anilinonaphthylsulphonic acid) in tris buffer of pH 7.2 are described for the stabilisation of POD conjugates; U.S. Pat. No. 4,757,016 describes aminopyrine, for example in phosphate, citrate or borate buffer; from U.S. Pat. No. 4,252,896 is known a medium containing ANS and serum protein; U.S. Pat. No. 4,448,882 describes a medium containing 4-aminoantipyrine, ANS and serum protein; and U.S. Pat. No. 4,169,012 describes the use of polyvalent ions of Groups 2 and 3 of the Periodic System. However, POD conjugates in solution can only be stabilised for a limited period of time with these additives. Even after a few days, a distinct decrease of the POD activity or of the stability is observed in immunological tests.

It is an object of the present invention to provide a solutions containing conjugates of POD and immunologically bindable substances with improved stability which can be stored at ambient temperature for a comparatively long period of time and which can be produced in a simple and reproducable way.

Thus, according to the present invention, there is provided a storable solution containing conjugates of POD and immunologically bindable substances, characterised by a pH value of 5.0 to 6.5, adjusted by means of an organic buffer substance with a concentration of 40 to 100 mmol/l, and 0.05 to 1.0 mol/l an aspartate salt.

As POD conjugates, there are preferably used the conjugates of POD as label and of a binder and especially immunological binder substance employed for immunological determination processes. As binder conjugate partners of POD, there are especially preferably used antibodies, fragments thereof, antigens, haptens, biotin and streptavidin.

According to the present invention, as organic buffer substance, it is especially preferred to use Good buffer, citrate buffer and/or 2-(N-morpholino)-ethanesulphonic acid (MES), MES being preferably used.

On the basis of the pH values to be adjusted to one another, of the concentration of the buffer substances and of the presence of the aspartate, outstanding stability results are achieved with the POD conjugate solutions according to the present invention.

In addition, the solutions according to the present invention preferably contain stabilisers, preserving agents and/or inert proteins, namely, especially 0 to 0.4 g/l of stabilisers, 0 to 1 g/l of preserving agents and/or 0 to 20 g/l of inert protein.

Inert proteins (supporting proteins) include, for example, albumins, casein and immunoglobulins. Stabilisers which can be used according to the present invention include, for example, ANS, phenol and dimethylaminoantipyrine. Preserving agents which can be used according to the present invention include, for example, KATHON (5-chloro-2-methyl-4-isothiazoline-3-one and 2-methyl-4-isothiazolin-3-one), OXIPYRION (2-hydroxypyridin-N-oxide) and methyl isothiazolone.

The solutions according to the present invention possess outstanding stabilities. For different POD conjugates, for example MAB-POD or hapten-POD, after storage for 3 weeks at 35° C., the peroxides activity is still 80 to 99% of the initial value.

The aspartate salt is preferably an alkali or alkaline earth metal salt. Ammonium aspartate can also be used. Especially preferred embodiments of the invention utilize either potassium aspartate or magnesium aspartate.

The following Examples are given for the purpose of illustrating the present invention, without limiting it thereto. If nothing otherwise is states, the percentages and parts are by weight.

EXAMPLE 1

Carrying Out of an Immunological Determination Process

The test was carried out according to the ELISA test principle as a one-step sandwich test by means of solid phase-bound streptavidin, a biotinylated, monoclonal antibody (MAB-Bi) and a peroxidase-labelled second monoclonal antibody (MAB-POD).

100 µl of sample and 1000 µl of working solution were introduced into a polystyrene test tube coated with streptavidin (production according to EP-A 0 269 092).

Composition of the POD Storage Solution

MAB-POD (POD activity: 20 U/ml)
40 mmol/l buffer (4-morpholinoethanesulphonic acid, phosphate buffer or citrate buffer) (pH value according to the following Table 1)
0.1 mol/l magnesium aspartate
0.2 g/l 4-dimethylaminoantipyrine
0.1 g/l OXIPYRION (2-hydroxypyridin-N-oxide)
10 g/l bovine immunoglobulin.

Composition of the Working Solution 1.5 µg/ml MAB-Bi
1/100th POD storage solution
Incubation was carried out for 1 hour at ambient temperature, followed by washing twice with 0.9% aqueous sodium chloride solution, whereafter 1000 µl of substrate solution were added thereto.

Substrate Solution 100 mmol/l phosphate-citrate buffer (pH 5.0)
1.47 mmol/l sodium perborate
9.1 mmol/l,2,2'-azino-di-(3-ethylbenzthiazoline-6-sulphonic acid) diammonium salt (ABTS®)

After incubation for 30 minutes, the colour formed was determined photometrically at 420 nm.

EXAMPLE 2

Determination of a Peroxidase Activity in MAB-POD Conjugates 2.9 ml of substrate solution and 0.1 ml of dilute sample (MAB-POD) were mixed in a cuvette with 1 cm path length and, after mixing, the absorption change was monitored at ambient temperature for 5 minutes at 405 nm.

An average value of the extinction change per minute was determined. The POD activity was determined according to the following equation:

$$activity = 0.8152 \times A/min \; (U/ml \text{ of sample solution})$$

EXAMPLE 3

Stability of Anti-TSH Antibody-POD Conjugate in Various Buffer Solutions

Anti-TSH antibody-POD conjugate was stored in POD storage solution (without the addition of MAB-Bi) at different pH values in different buffer substances for 3 weeks at 4° C. and 35° C.

The function of the conjugate was tested according to the process described in Example 1 in the presence of buffer and magnesium aspartate. The POD activity was also tested according to Example 2.

The following Table 1 shows the results obtained:

TABLE 1

|  | activity after storage for | | | |
|---|---|---|---|---|
|  | 3 weeks at 4° C. | | 3 weeks at 35° C. | |
| buffer ion, pH | immune activity | POD activity | immune activity | POD activity |
| acetate, pH 6.0 | 100% | 100% | 87% | 90% |
| phosphate, pH 6.0 | 100% | 100% | 78% | 100% |
| MES, pH 6.5 | 100% | 100% | 87% | 100% |
| MES, pH 6.0 | 100% | 100% | 87% | 100% |
| MES, pH 5.0 | 100% | 100% | 82% | 100% |
| MES, pH 4.0 | 100% | 100% | 43% | n.d. |
| phosphate, pH 8.0 | 100% | 100% | 62% | 100% | n.d. = not determined

Table 1 shows that admittedly the POD activity is still present after storage for 3 weeks at 35° C. but small losses in the activity are only seen when the pH value of the buffer is from 5 to 6.5.

EXAMPLE 4

Influence of Magnesium Aspartate

As described in Example 3, anti-TSH antibody-POD conjugate (activity 20 U/ml in 40 mmol/ml 4-MES buffer at pH 6.0) was stored in the presence of different magnesium aspartate concentrations.

The stability of the solutions was tested after 3 weeks storage in a test according to Example 1. The following Table 2 shows the results obtained:

TABLE 2

| magnesium aspartate | activity after storage for | |
|---|---|---|
| concentration | 3 weeks at 4° C. | 3 weeks at 35° C. |
| 0.00 mol/l | 100% | 64% |
| 0.05 mol/l | 100% | 84% |
| 0.10 mol/l | 100% | 77% |
| 0.25 mol/l | 100% | 81% |

Table 2 shows that magnesium aspartate has a positive influence on the performance of the anti-TSH antibody conjugates.

EXAMPLE 5

Influence of Buffer Solutions with a pH Value of from 5.5 to 6.0 on the Stability of Different POD Conjugates The POD-hapten and antibody conjugates mentioned in Table 3, with an average enzymatic activity of 0.4 to 20 U/ml, were stored for 3 weeks at 4° C. and 35° C. in a solution of 40 mmol/l 4-MES(pH 5.0 to 6.0), 0.1 g/l oxipyrion and 10 g/l bovine immunoglobulin. Subsequently, an appropriate function test for the antigen was carried out analogously to Example 1. The following Table 3 shows the results obtained:

TABLE 3

| POD conjugate with | activity after storage for | |
|---|---|---|
| 0.1 mol/l aspartate | 3 weeks 4° C. | 3 weeks 35° C. |
| anti-TSH MAB-POD | 100% | 85% |
| anti-TSH-PAB-POD | 100% | 89% |
| anti-LH MAB-POD | 100% | 86% |
| anti-FSH MAB-POD | 100% | 84% |
| anti-HCG MAB-POD | 100% | 79% |
| anti-CEA MAB-POD | 100% | 77% |

EXAMPLE 6

Influence of Potassium Aspartate

The parameters of example 4 were followed, with one exception. Rather than the magnesium salt, a solution of potassium aspartate (0.24 mole/l) was used. Again, using all parameters of Example 4, immune activity was checked after three weeks storage at 4° C. The activity was 100%. After three weeks at 35° C., the immune activity was found to be 87%.

The foregoing demonstrates the usefulness of aspartate salts in stabilizing the immune activity of conjugates of peroxidase and immunologically bindable substances. Thus, in its broadest embodiments the invention relates to stabilized compositions which comprise at least one conjugate of peroxidase and an immunologically bindable component, an organic buffer at a concentration of from about 40 to about 100 mmol/l, and an aspartate salt at a concentration of from about 0.05 to about 1.0 mol/l. The composition is in the form of a solution and has a pH of from about 5.0 to about 6.5. Preferred aspartate salts are alkali metal, alkaline earth metal, and ammonium salts. Especially preferred are compositions comprising one of magnesium aspartate or potassium aspartate. Preferred organic buffers are GOOD buffer, citrate buffer, or MES (i.e., 2-(N-morpholino)-ethane sulphonic acid). The compositions may contain additional ingredients, including stabilizers, preserving agents, and insert proteins. Stabilizers, when used are preferably used at concentrations up to about 0.4 g/l. When preserving agents are used, concentrations up to about 0.1 g/l are preferred. Insert proteins, when present, are used at concentrations up to about 20 g/l.

Examples of suitable stabilizers are anilinonapthyl sulphonic acid, phenol, or dimethyl amino antipyrene. Preferred preservatives are KATHAN, OXYPYRION, or methylisothiazoline, and the inert protein is preferably albumin, casein, or immunoglobulin. The immune component, i.e., the immunologically bindable substance, includes any and all of the materials recognized as such by the art, including antibodies, antibody fragments, such as Fab fragments, antigens, haptens, biotin, avidin, and streptavidin. Other aspects of the invention will be clear to the skilled artisan and need not be set forth here.

It will be understood that the specification and examples are illustrative but not limitative of the present invention and that other embodiments within the spirit and scope of the invention will suggest themselves to those skilled in the art.

We claim:

1. Stabilized composition comprising:
   (i) a conjugate of peroxidase and an immunologically bindable substance;
   (ii) an organic buffer substance at a concentration of from about 40 to about 100 mmol/l; and
   (iii) an aspartate salt at a concentration of from about 0.05 to about 1.0 mol/l, wherein said stabilized composition is in the form of a solution and has a pH of from 5.0 to 6.5.

2. The stabilized composition of claim 1, wherein said aspartate salt is an alkali metal salt.

3. The stabilized composition of claim 1, wherein said aspartate salt is an alkaline earth metal salt.

4. The stabilized composition of claim 1, wherein said aspartate salt is ammonium aspartate.

5. The stabilized composition of claim 1, wherein said aspartate salt is potassium aspartate.

6. The stabilized composition of claim 1, wherein said aspartate salt is magnesium aspartate.

7. The stabilized composition of claim 1, wherein said organic buffer substance comprises GOOD buffer, a citrate buffer, or 2-(N-morpholino)-ethanesulphonic acid (MES).

8. The stabilized composition of claim 7, wherein said organic buffer is MES.

9. The stabilized composition of claim 1, further comprising a stabilizer, a preserving agent, or an inert protein.

10. The stabilized composition of claim 9, comprising a stabilizer at a concentration up to about 0.4 g/l.

11. The stabilized composition of claim 9, comprising a preserving agent at a concentration up to about 1 g/l.

12. The stabilized composition of claim 9, comprising an inert protein at a concentration up to about 20 g/l.

13. The stabilized composition of claim 9, wherein said stabilizer is anilinonaphthyl sulphonic acid, phenol, or dimethylaminoantipyrene.

14. The stabilized composition of claim 9, wherein said preservative is KATHON (5-chloro-2methyl-4-isothiazoline- 3-one and 2-methyl-4-isothiazolin-3-one), OXIPYRION (2-hydroxypyridin-N-oxide) or methylisothiazoline.

15. The stabilized composition of claim 9, wherein said inert protein is an albumin, casein, or an immunoglobulin.

16. The stabilized composition of claim 1, wherein said bindable substance is an antibody, an antibody fragment, an antigen, a hapten, biotin, or streptavidin.

17. The stabilized composition of claim 16, wherein said antibody is a monoclonal antibody.

* * * * *

UNITED STATES PATENT AND TRADEMARK OFFICE
CERTIFICATE OF CORRECTION

PATENT NO. : 5,460,944
DATED : April 21, 1993
INVENTOR(S) : Norbert Franken, et. al.

It is certified that error appears in the above-indentified patent and that said Letters Patent is hereby corrected as shown below:

Title page, item [21], change "Appln. No." from "51,253" to --51,263--.

Signed and Sealed this

Twenty-ninth Day of July, 1997

Attest:

Attesting Officer

BRUCE LEHMAN

Commissioner of Patents and Trademarks